(12) United States Patent
Shampine et al.

(10) Patent No.: US 11,471,042 B2
(45) Date of Patent: Oct. 18, 2022

(54) VISION SCREENING APPARATUS WITH A VISUAL ACUITY PROTOCOL COMPLIANCE FEATURE AND AN ASSOCIATED METHOD OF VISION SCREENING

(71) Applicant: Welch Allyn, Inc., Skaneateles Falls, NY (US)

(72) Inventors: William Shampine, Syracuse, NY (US); Jennifer Bergstrom, Portland, OR (US); Kathryn M. Coles, Syracuse, NY (US); David L. Kellner, Baldwinsville, NY (US); John A. Lane, Weedsport, NY (US); Megan Schneider, Skaneateles Falls, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 507 days.

(21) Appl. No.: 16/515,495

(22) Filed: Jul. 18, 2019

(65) Prior Publication Data

US 2021/0015358 A1 Jan. 21, 2021

(51) Int. Cl.
*A61B 3/032* (2006.01)
*A61B 3/00* (2006.01)
(Continued)

(52) U.S. Cl.
CPC ............ *A61B 3/032* (2013.01); *A61B 3/0041* (2013.01); *G06F 3/011* (2013.01); *G06F 3/017* (2013.01); *G06V 40/19* (2022.01); *G06V 40/197* (2022.01)

(58) Field of Classification Search
CPC ....... A61B 3/032; A61B 3/0041; G06F 3/011; G06F 3/017; G06V 40/19; G06V 40/197
(Continued)

(56) References Cited

U.S. PATENT DOCUMENTS 5,682,144 A   10/1997  Mannik
5,914,772 A *  6/1999  Dyer ...................... A61B 3/028
                                                351/222
(Continued)

FOREIGN PATENT DOCUMENTS

CN    108523837 A    5/2018
CN    208176544 U   12/2018
(Continued)

OTHER PUBLICATIONS

An Interactive Interface for Remote Administration of Clinical Tests Based on Eye Tracking; A. Faro, D. Giordano, C. Spampinato, D. De Tommaso, S. Ullo; Department of Inormatics and Telecommunication Engineering University of Catania, Catania, 95125, Italy; ETRA 2010, Austin, TX, Mar. 22-24, 2010; pp. 69-72.
(Continued)

*Primary Examiner* — Mohammed A Hasan
(74) *Attorney, Agent, or Firm* — Lee & Hayes, P.C.

(57) ABSTRACT

A vision screening apparatus includes first and second display units, a processor, and instructions which are executable by the processor. The instructions, when executed by the processor, cause the apparatus to 1) carry out a photorefraction test of a subject, 2) estimate the subject's visual acuity based on the photorefraction test, 3) present the subject with a visual acuity check optotype for an interval of time, and 4) monitor for noncompliance with a visual acuity check protocol during at least part of the time interval.

19 Claims, 11 Drawing Sheets

(51) Int. Cl.
*G06F 3/01* (2006.01)
*G06V 40/19* (2022.01)
*G06V 40/18* (2022.01)

(58) Field of Classification Search
USPC .......................................................... 359/222
See application file for complete search history.

(56) References Cited

U.S. PATENT DOCUMENTS

| | | |
|---|---|---|
| 8,226,237 B2 | 7/2012 | Mandelstam-Manor et al. |
| 8,599,020 B2 | 12/2013 | Koike |
| 9,237,846 B2 | 1/2016 | Mowrey et al. |
| 9,402,538 B2 | 8/2016 | Mowrey et al. |
| 9,408,535 B2 | 8/2016 | Mowrey et al. |
| 9,439,593 B2 | 9/2016 | Shepherd et al. |
| 9,962,119 B2 | 5/2018 | Macknik et al. |
| 2013/0141694 A1* | 6/2013 | Seriani ................... A61B 3/18 351/204 |
| 2014/0129259 A1* | 5/2014 | Seriani ................... G16H 80/00 705/3 |
| 2016/0120402 A1* | 5/2016 | Limon .................. A61B 3/0058 351/239 |
| 2017/0027440 A1 | 2/2017 | Mowrey et al. |
| 2019/0125183 A1 | 5/2019 | Lane et al. |

FOREIGN PATENT DOCUMENTS

| | | |
|---|---|---|
| CN | 109711309 A | 5/2019 |
| JP | 4692526 B2 | 6/2011 |
| JP | 5714949 B2 | 5/2015 |

OTHER PUBLICATIONS

Journal of Mobile Technology in Medicine; Validation of Portable Electronic Visual Acuity System; Pavindran A. Gounder, MBBS; Eliza Cole, MBBS; Stephen Colley, MBBS; Franzco, David M Hille, Msc(Oxon); corresponding author: Pav Gounder; vol. 3, issue 2, Jul. 2014; pp. 35-39.

* cited by examiner

VISION SCREENING APPARATUS WITH A VISUAL ACUITY PROTOCOL COMPLIANCE FEATURE AND AN ASSOCIATED METHOD OF VISION SCREENING

CROSS REFERENCE TO RELATED APPLICATIONS

This application is related to U.S. Pat. No. 9,237,846 Entitled "Photorefraction Ocular Screening Device and Methods" issued on Jan. 19, 2016, and U.S. application Ser. No. 16/175,249 entitled "Visual Acuity Examination" published as US 2019/012 5183, the contents of both of which are incorporated herein by reference.

TECHNICAL FIELD

The subject matter described herein relates to a vision screening apparatus having safeguards for ensuring the quality of a visual acuity check conducted with the apparatus and to methodology of visual acuity screening using the apparatus.

BACKGROUND

U.S. Pat. No. 9,237,846 describes a photorefraction ocular screening device which includes the capability to detect the pupils of a subject undergoing a vision screening and to estimate and report the refractive error of the subject's eyes. The device also determines and reports a recommended refractive error correction expressed in diopters. The reports of refractive error and recommended correction appear on a display unit which faces the examiner, i.e. the operator of the device.

The device, however, does not provide a true determination of the subject's actual visual acuity. This is because the refractive error estimated by the device accounts only for the optical properties of the subject's cornea, lens, and vitreous humor. It does not and cannot evaluate whether other elements of the person's visual faculties are functioning properly. As a result, a subject could have compromised vision despite having little or no refractive error. In short, the estimated refractive error, standing alone, could be misleading as to the subject's actual visual acuity.

The device described in US 2019/0125183 improves upon the device of U.S. Pat. No. 9,237,846 by including a simplified visual acuity assessment. The '183 device includes a second display unit that faces the subject. Referring to FIG. 5 of the '183 publication, the device conducts a photorefraction test, which results in an estimate of the subject's visual acuity. The device then presents the subject with an optotype corresponding to the estimate of the subject's visual acuity. If the subject can correctly report the optotype to the examiner (to the examiner's satisfaction) the photorefractive estimate of the subject's visual acuity is considered to have been confirmed. However if the subject cannot successfully report the optotype to the examiner, then the examiner may be justified in questioning the visual acuity estimate derived from the photorefractive test, and repeat the test or refer the subject to another professional for a more comprehensive and rigorous examination.

By using an optotype corresponding to the estimated visual acuity, rather than having the subject proceed line by line through a conventional eye chart with lines of diminishing character size, the '183 device is time efficient, making it possible to screen a large population of subjects in a short time.

As part of the protocol for conducting the visual acuity check the subject may be asked to attempt to read the optotype first with one eye occluded and then with the other eye occluded. Occluded means that the eyelid is closed, or that the subject is covering the eye with his hand or a paddle-like device. The protocol may also include instructing the subject to refrain from squinting in an attempt to see the optotype more clearly. Another protocol may call for the subject to use both eyes, but again may prohibit the subject from squinting.

In some cases the subject may intentionally or unintentionally fail to comply with the protocol. For example the subject may fail to completely occlude one eye, or may squint during either a monocular or binocular test. The examiner may not notice that the subject is not in compliance with the protocol. As a result, the examination may lead to a falsely favorable assessment of the subject's actual visual acuity.

One additional issue of concern is that the subject may have an abnormality that, for some other subject, would be correctly identified as a noncompliance but which is characteristic of the subject undergoing examination. For example the subject may have a droopy eyelid or eyelids that partially obscure the pupil or otherwise cause the eye to be in a state that, for a different subject, would be consistent with or suggestive of noncompliance. The subject may therefore be judged to be in a state of noncompliance with the protocol when, in fact, he is in a state of compliance.

It is, therefore, desirable to provide a way to identify a noncompliance with a visual acuity check protocol during use of an apparatus of the type described in the '183 publication. It is also desirable to guard against falsely reporting noncompliance in subjects who are in a compliant state, but who have an abnormality that mimics noncompliance.

SUMMARY

A vision screening apparatus includes first and second display units, a processor, and instructions which are executable by the processor. The instructions, when executed by the processor, cause the apparatus to 1) carry out a photorefraction test of a subject, 2) estimate the subject's visual acuity based on the photorefraction test, 3) present the subject with a visual acuity check optotype for an interval of time, and 4) monitor for noncompliance with a visual acuity check protocol during at least part of the time interval.

BRIEF DESCRIPTION OF THE DRAWINGS

The foregoing and other features of the various embodiments of the apparatus and methodology described herein will become more apparent from the following detailed description and the accompanying drawings in which.

DETAILED DESCRIPTION

Figure 1:
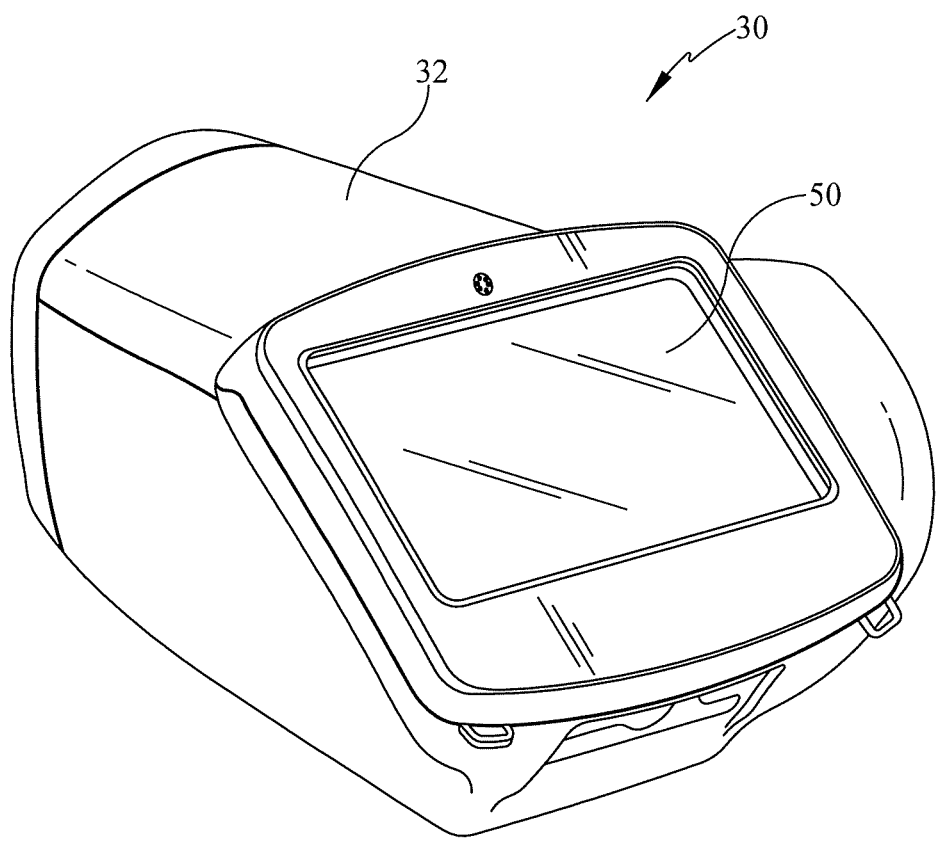
FIG. 1 is a perspective view of a vision screening apparatus having a housing and showing a first display unit which is intended to face an examiner during his use of the device.

The present invention may comprise one or more of the features recited in the appended claims and/or one or more of the following features or combinations thereof.

In this specification and drawings, features similar to or the same as features already described may be identified by reference characters or numerals which are the same as or similar to those previously used. Similar elements may be identified by a common reference character or numeral, with suffixes being used to refer to specific occurrences of the element.

Figure 2:
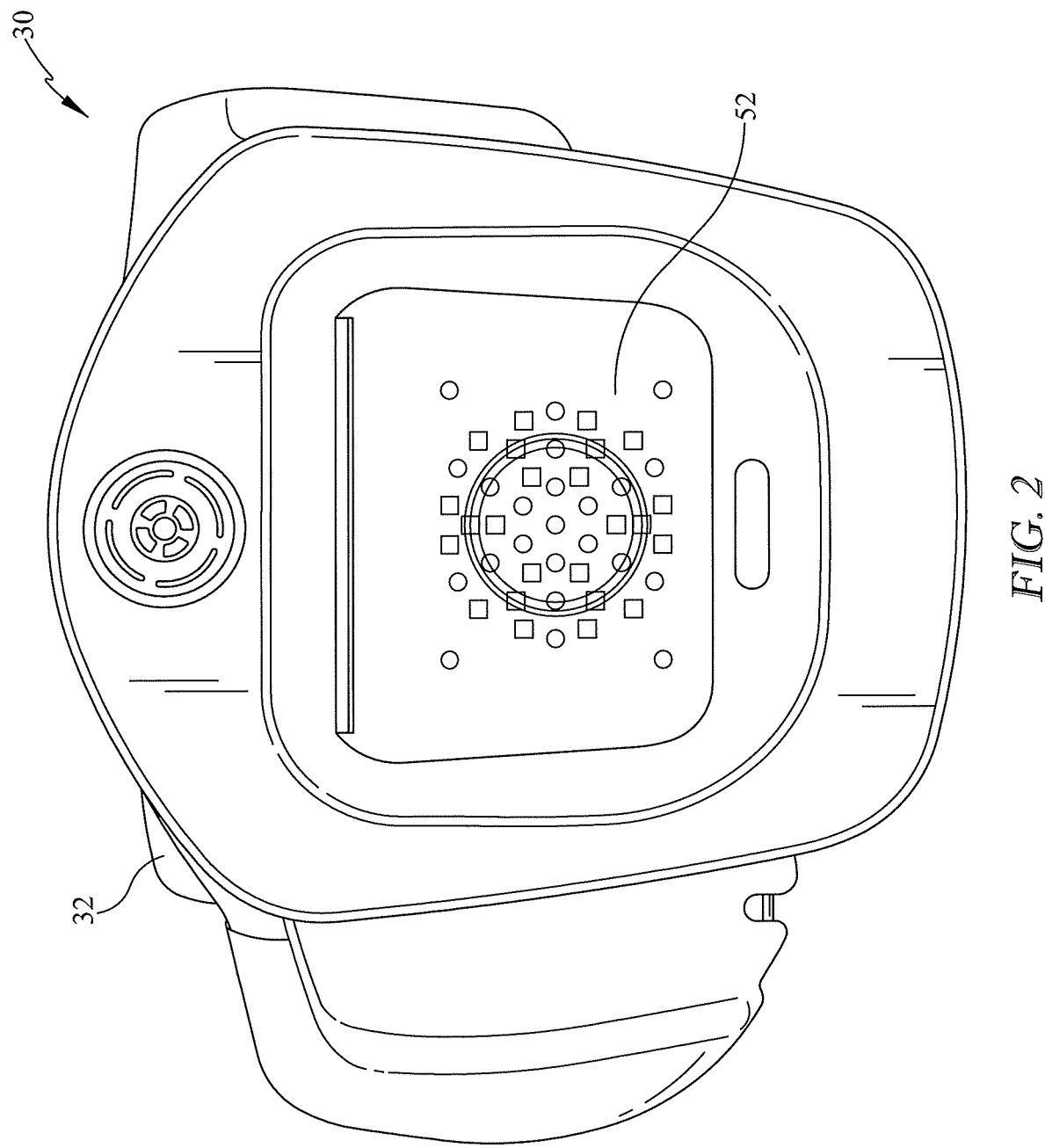
FIG. 2 is an end view of the apparatus of FIG. 1 showing a second display unit which is intended to face a subject during a vision screening of the subject.
Figure 3:
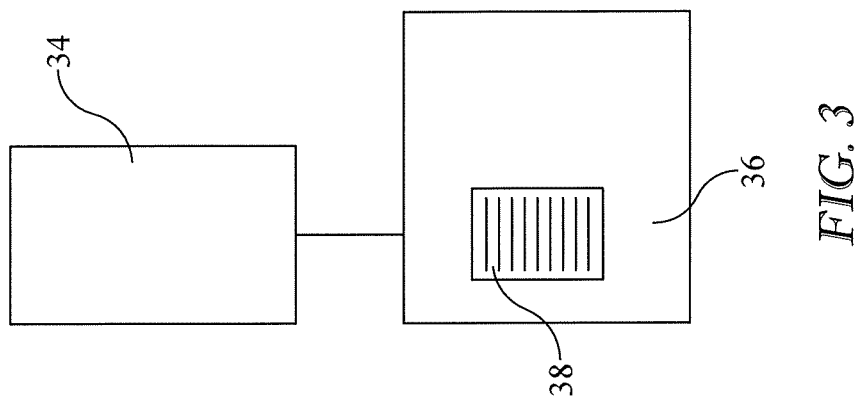
FIG. 3 is a schematic view of selected components of the apparatus of FIG. 1, in particular a processor or controller and a memory which holds processor executable instructions.

Referring to FIGS. 1-3, a photorefraction apparatus 30 for carrying out a vision screening includes a housing 32 containing the various components necessary to conduct a vision examination on a subject as described in U.S. Pat. No. 9,237,846 and US 2019/0125183. These include a processor 34, and a memory 36 which holds instructions 38 which are executable by the processor.

Figure 4:
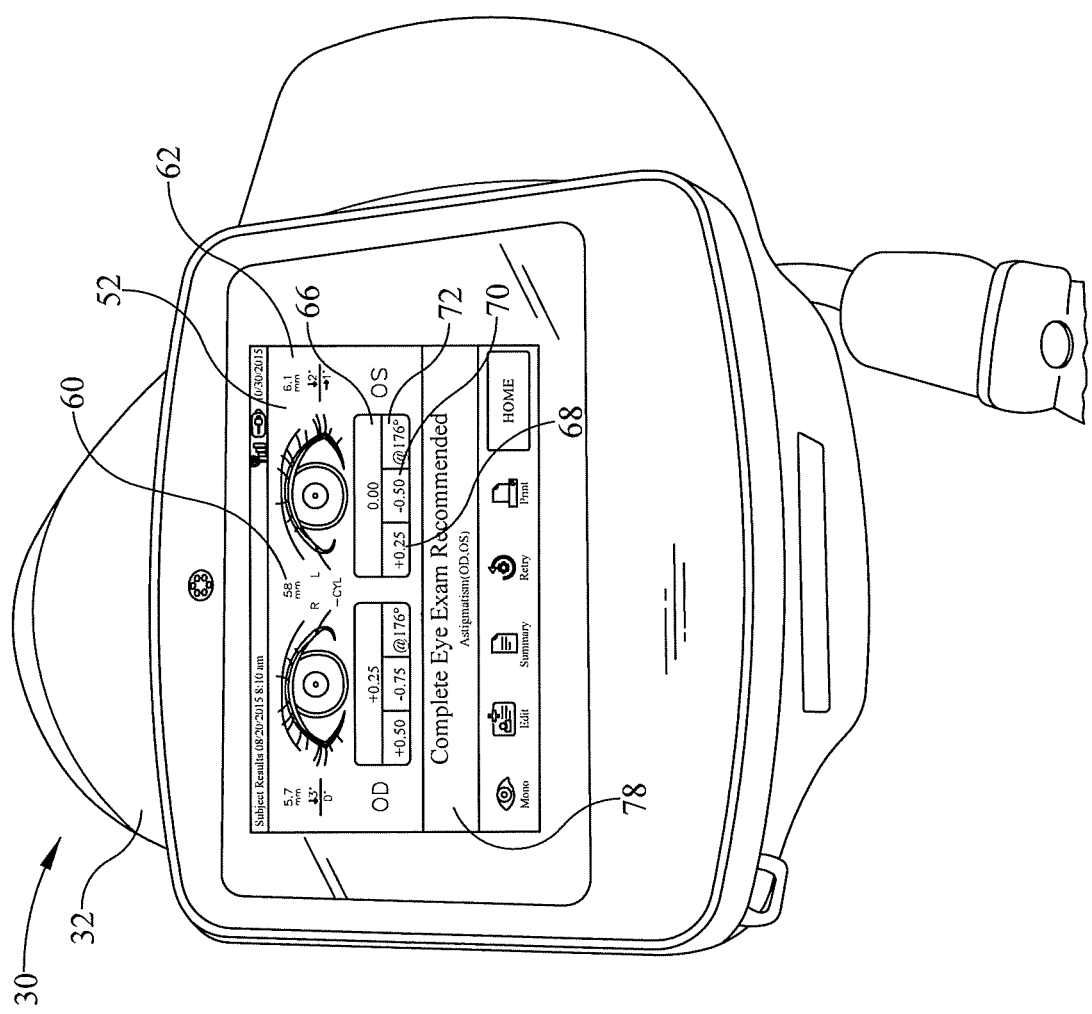
FIG. 4 is an end view of the first display unit of FIG. 1 showing an example of information that may be displayed on the first display unit.

Referring additionally to FIG. 4, the first display reports information about results of the vision screening to the examiner. The information depicted in FIG. 4 includes pupillary distance 60, pupil size 62, refraction parameters (spherical equivalent 66, sphere 68, cylinder 70 and axis 72) and the overall findings of the screening 78.

The apparatus also includes a second display unit 52 on a subject facing side thereof. The second display is adapted to present the subject with an optotype. This specification uses "optotype" to refer to both individual symbols and to collections of symbols such as one or more lines of letters, numbers, or other symbols of the type present on an eye chart such as a Snellen chart or a logMAR chart. As explained in more detail later in this specification, at least some embodiments of apparatus 30 display only a single symbol, a single line of symbols, or some other subset of the symbols typically present on a standard eye examination chart.

Figure 5:
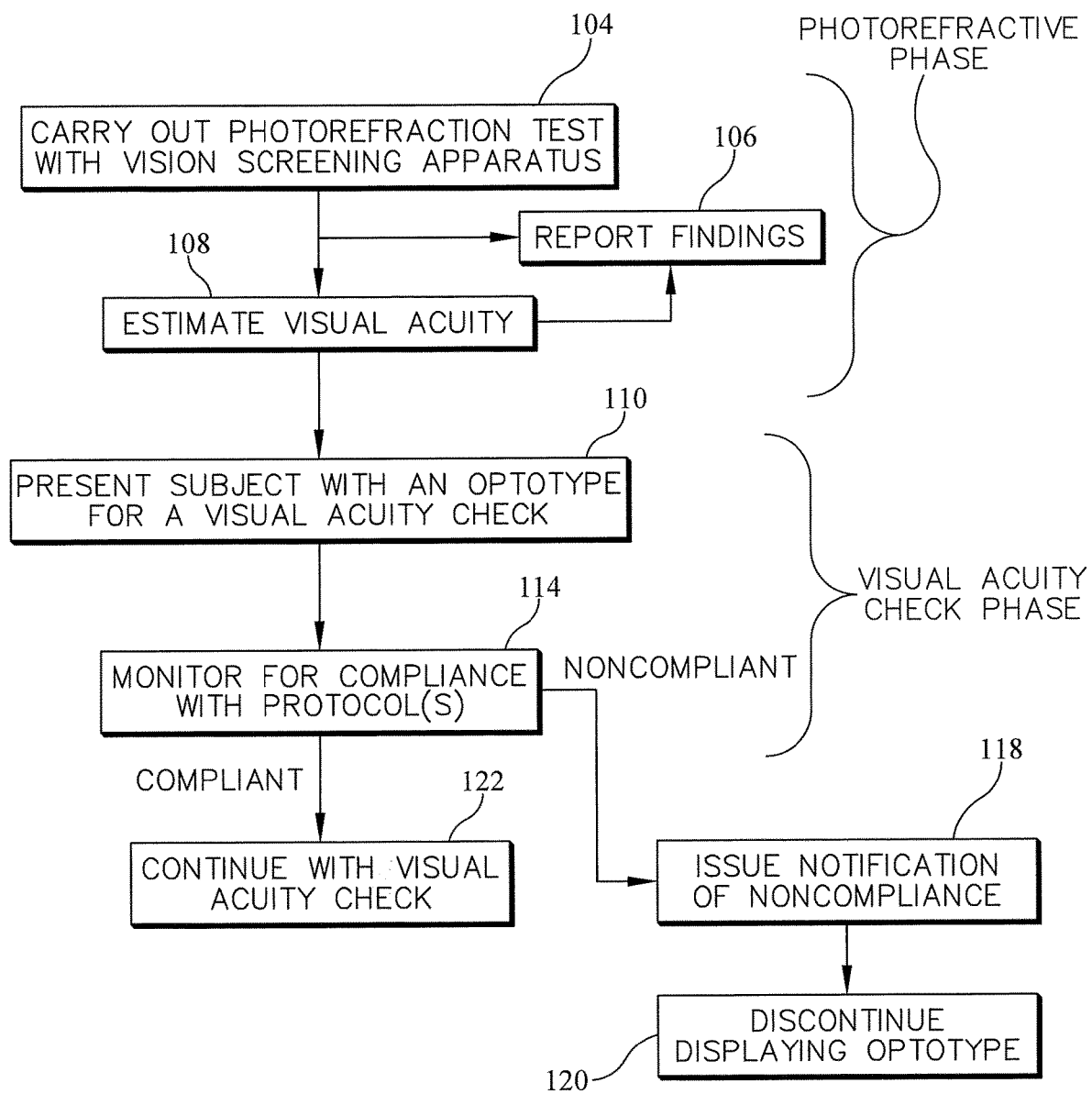
FIG. 5 is a diagram illustrating operation of the apparatus of FIGS. 1, 2 and 4 in response to execution of the instructions of FIG. 3 by the processor of FIG. 3, including monitoring for and identifying noncompliance with a protocol during a visual acuity phase of a vision screening and issuing a notice of the noncompliance if a noncompliance occurs.

Referring to FIG. 5, instructions 38, when executed by processor 34, cause the apparatus to carry out a photorefraction test of the subject (block 104) and to report information about the findings of the photorefractive test to the examiner (block 106) by displaying those findings (e.g. parameters 60, 62, 66, 68, 70, 72, 78) on the first display unit. The apparatus also estimates the subject's visual acuity based on the information gathered during the photorefraction test (block 108). The estimate of the subject's visual acuity may be among the findings displayed on the first display unit. One well known expression of visual acuity includes the 20/10, 20/20, 20/40, 20/100 designations indicating the subject's visual acuity in comparison to "normal" visual acuity. One other expression of visual acuity is the diopter value (inverse of focal length in meters) necessary to correct the person's vision.

The foregoing actions, namely carrying out a photorefraction test and estimating the subject's visual acuity based on the photorefraction test, may be referred to as the photorefraction or photorefractive phase of operation. Subsequent actions, namely presenting the subject with an optotype and monitoring for compliance with a visual acuity check protocol, which are described in more detail below, may be referred to as the visual acuity check phase, or simply visual acuity phase of operation.

If the photorefraction test findings are that the subject suffers from a significant refractive error (e.g. 20/80 or worse), the examiner may choose to terminate the screening and refer the subject to another professional for a more comprehensive and rigorous examination. Otherwise the apparatus proceeds with the visual acuity check phase of the screening.

In the visual acuity check phase the instructions cause the apparatus to present the subject with a visual acuity check optotype (block 110) by displaying the optotype on the second display unit for some interval of time. The subject is asked to report what he perceives to the examiner in order to check the visual acuity estimate obtained by the photorefraction test at block 108. The subject's perception, in comparison to what the display is actually presenting, enables the examiner to assess the validity of the photorefractive estimate of the subject's visual acuity obtained from the photorefraction test.

During at least part of the time interval that the visual acuity check is taking place the instructions cause the apparatus to monitor for noncompliance with a visual acuity check protocol (block 114). The noncompliance may be intentional on the part of the subject or may be unintentional. One form of noncompliance is the subject's use of both eyes to discern the optotype despite having been instructed to use only one eye. The apparatus determines if more than one eye is in use by analyzing an image it has captured and determining if one or two pupils is present in the captured image.

Another form of noncompliance is the subject squinting in order to discern the optotype. The apparatus determines if the subject is squinting by analyzing an image it has captured and determining if a pupil or pupils present in the image is/are of approximately normal circular shape (in which case the subject is likely not squinting) or is/are distorted, for example due to being irregularly shaped (in which case it is more likely that the subject is squinting).

If a noncompliance is identified the executed instructions cause the apparatus to issue a notification of noncompliance (block 118). The notification may take any suitable form such as a visual notification displayed on the first display unit or a light on the apparatus housing or an aural signal. The notification of noncompliance may include a notice of the reason for noncompliance (e.g. subject is using both eyes instead of one or subject is squinting). Two or more different forms of notification can be used in combination with each other. In addition to causing the apparatus to issue a notification of noncompliance, the instructions may also cause the apparatus to discontinue displaying the optotype (block 120). Discontinuing the optotype display marks the end of, or at least an interruption of, the visual acuity phase of operation.

The notification of noncompliance alerts the examiner that some corrective action needs to be taken, such as counseling the subject to not squint or that he has not covered one of his eyes adequately. Referring now to the embodiment of FIG. 6, instructions 38 may be written so that they cause the apparatus to resume the visual acuity phase of operation in response to an indication from the examiner that the noncompliance has be remedied. Such indication may be made by a touch sensitive option (e.g. a "RESUME" button) displayed on first display unit 50 as a result of a noncompliance having been identified. The "RESUME" instructions cause the operation of the apparatus to branch from block 120 to block 110 and perform the presenting and monitoring operations of blocks 110, 114 without first repeating the carrying out and estimating operations of block 104, 108.

If noncompliance is not identified (expressed in FIGS. 5 and 6 as "Compliant") the executed instructions cause the apparatus to continue with the visual acuity check (block 122), i.e. to continue displaying the optotype.

If the photorefractor estimate and the optotype check yield similar outcomes (e.g. the same visual acuity assessment within some tolerance) the examiner can be more confident of the photorefraction test results than if the two assessments are highly dissimilar (e.g. outside the tolerance). If the photorefractor estimate and the optotype check yield dissimilar outcomes, the examiner may be justified in questioning whether the photorefraction based visual acuity estimate is a valid portrayal of the subject's actual visual acuity. (In some cases, however, dissimilar results may indicate some other problem, such as a neurological problem. For example the subject may be able to see the optotype clearly, but sees it reversed left to right or top to bottom)

Figure 7:
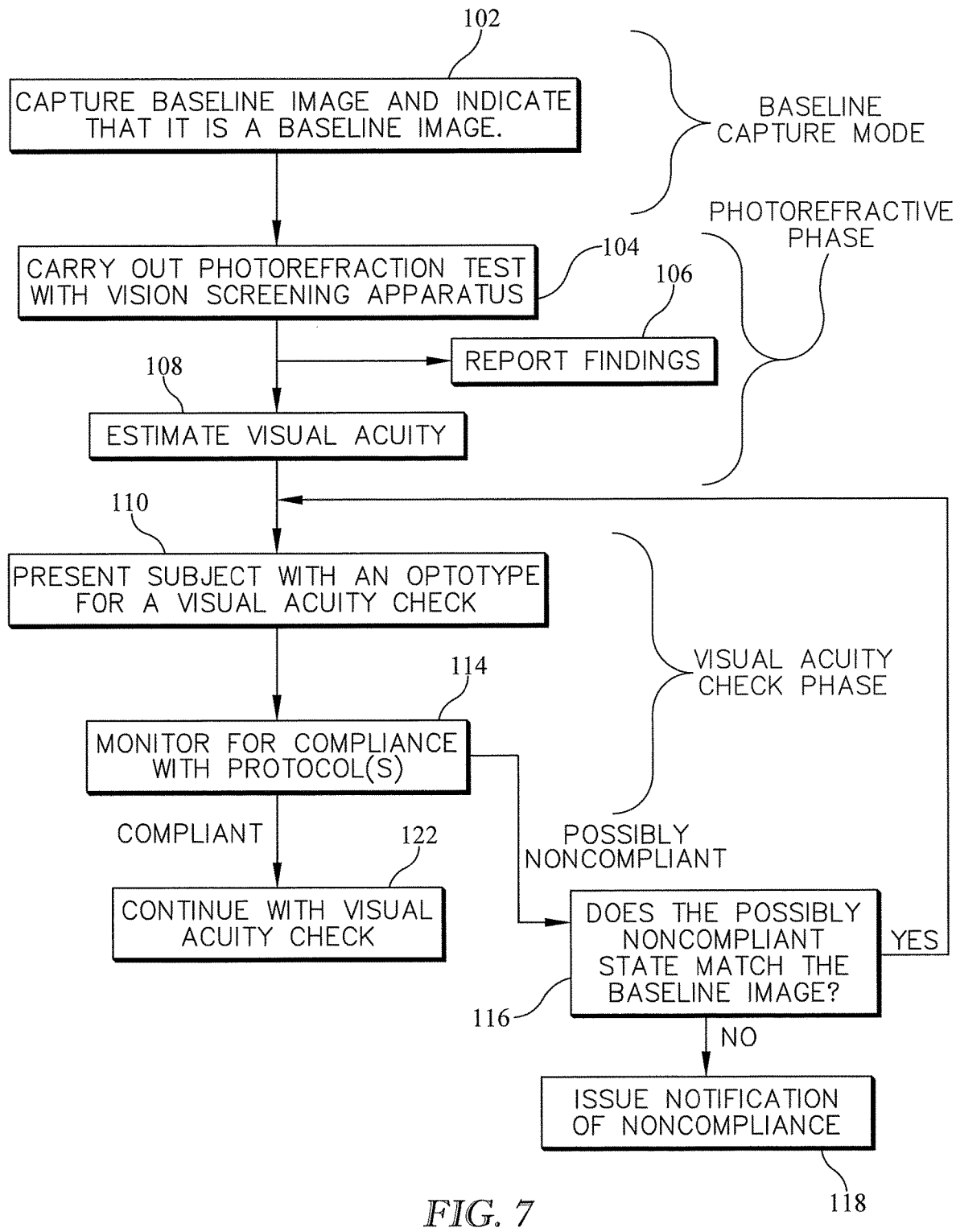
FIG. 7 is a diagram similar to FIG. 5 illustrating operation of an embodiment which refrains from identifying noncompliance in an image that might otherwise be consistent with or at least suggestive of noncompliance.

Referring to FIG. 7, in one embodiment the instructions adapt the apparatus to refrain from identifying noncompliance in an image that might otherwise be consistent with or at least suggestive of noncompliance. For example, the examiner may realize that a subject has an abnormality that would be correctly identified as a noncompliance in other subjects but is a characteristic of the subject presently of interest. One example is the droopy eyelid or eyelids condition mentioned in the Background section of this specification. As illustrated in FIG. 7, the apparatus has a mode of operation that permits the examiner to capture a baseline image of the subject's pupil or pupils and to indicate its status as a baseline image to the apparatus (block 102). For example the first display unit may include a touch sensitive menu or menus which enables the examiner to activate a baseline image capture mode, acquire the baseline image (which may be written to memory 36 for future reference), and exit the baseline image capture mode. Instructions 38 cause the apparatus to recognize the baseline image as characteristic of the subject With the baseline image having been established the instructions cause the apparatus to carry out a photorefraction test, estimate the subject's visual acuity based on the photorefraction test, present the subject with a visual acuity check optotype, and monitor for noncompliance, all as already described except that an indication of noncompliance at block 114 is treated as a possible noncompliance rather than a definite noncompliance. The executed instructions cause the apparatus to distinguish between actual noncompliance and false noncompliance by assessing whether or not the non-baseline image matches, within a specified tolerance, the baseline image previously acquired (block 102). If the images match, the instructions cause the apparatus to refrain from identifying the possible noncompliance in the non-baseline image as an actual noncompliance. Instead the instructions cause the apparatus to continue the visual acuity check (block 110) including monitoring for noncompliance (block 114). If the images do not match, the executed instructions cause the apparatus to treat the possible noncompliance as a genuine noncompliance (block 118).

FIG. 7 shows the baseline image being captured prior to carrying out the photorefraction test. Alternatively, the baseline image may be captured at any time that would make it available for guarding against an erroneous identification of noncompliance.

Figure 8:
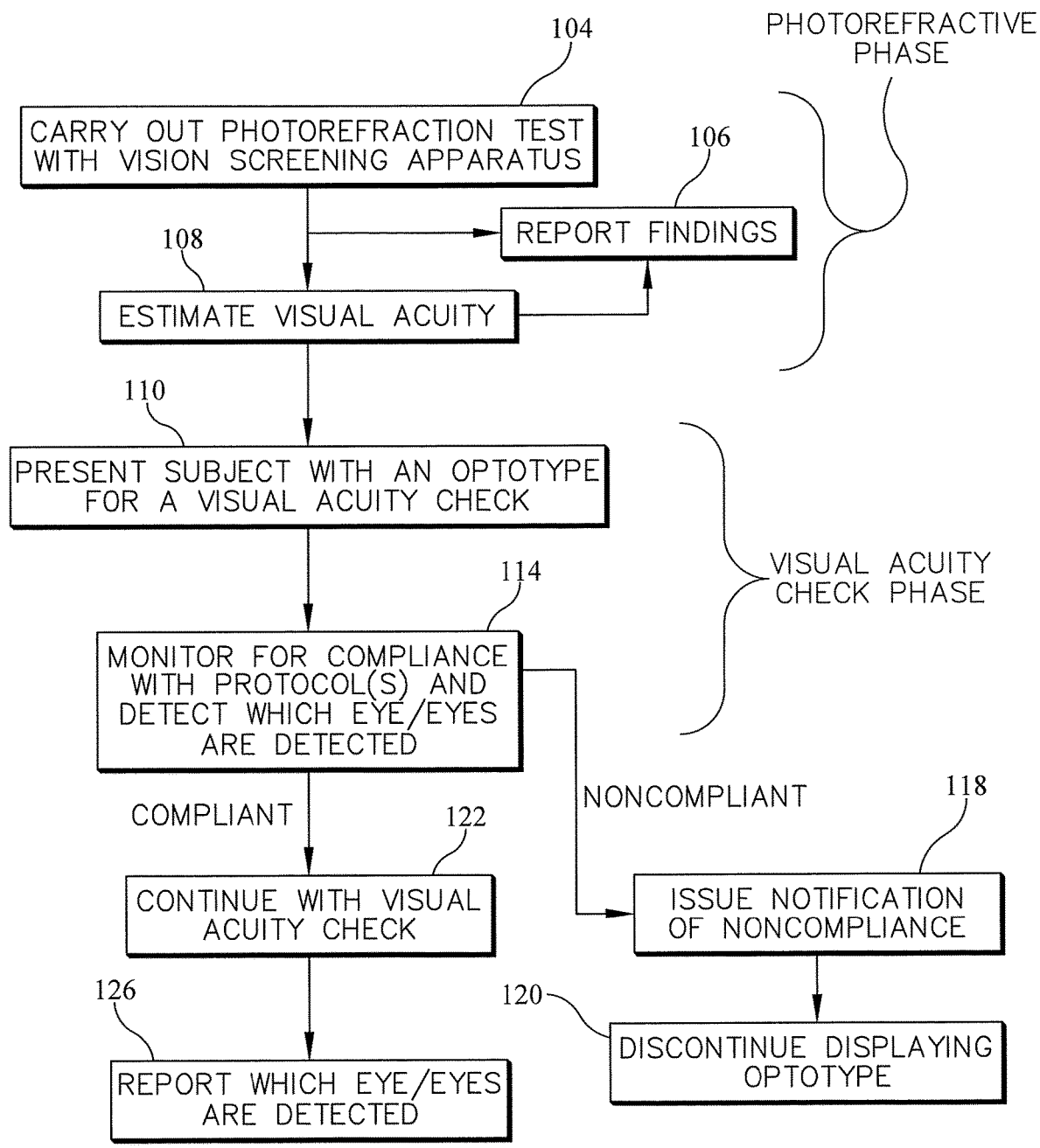
FIG. 8 is a diagram similar to FIG. 5 illustrating operation of an embodiment which identifies whether the apparatus detects one or two of the subject's eyes and, if only one eye, which one, and may also report if the one detected eye is the "correct" eye (left or right) during a monocular examination.

FIG. 8 shows an embodiment in which the executed instructions cause the apparatus to determine which of the subject's two eyes, left or right, is under examination. Blocks 104 through 110 are the same as in FIG. 5. Block 114 combines the action of monitoring for compliance with the additional action of using the apparatus's pupil detection capability to determine if the image includes one or two pupils, and if it contains only one pupil, which one (left or right). This functionality can be useful in the absence of a procedure which spells out the order in which each of the two eyes are to be examined during a monocular examination because the apparatus itself makes that determination and can write it to memory 36. This functionality can also be useful even if a standard procedure is being followed (e.g. left eye first, right eye second) because it can detect if the subject is covering the wrong eye during a monocular examination. At block 126 the apparatus reports the results, for example by displaying a message on display unit 50.

The optotype presented at block 110 of the diagrams may be a complete eye chart displayed in its entirety. The subject is asked to read the chart starting with a line of larger size symbols and to progress through lines of successively smaller symbols until he is no longer able to correctly identify the symbols to the examiner. His visual acuity based on the visual acuity check corresponds to the line of smallest symbols he can correctly report to the examiner. If the results of the visual acuity check match the findings of the photorefraction test, the findings of the photorefraction test are considered to have been confirmed. If not, the visual acuity estimated from the photorefraction test may not be a valid estimate, and the subject can be re-examined or referred for a more thorough and rigorous examination.

The displayed optotype may instead be only the portion of an eye chart whose lines correspond to visual acuity no worse than the estimated visual acuity based on the photorefraction test. The subject is asked to read the line of largest size symbols (or the symbol). If he can do so to the examiner's satisfaction the findings of the photorefraction test are considered to have been confirmed. If not, the visual acuity estimated from the photorefraction test may not be a valid estimate, and the subject can be re-examined or referred for a more thorough examination.

The displayed optotype may instead be only the one line of an eye chart corresponding to the estimated visual acuity based on the photorefraction test. The subject is asked to read the line. If he can do so to the examiner's satisfaction the findings of the photorefraction test are considered to have been confirmed. If not, the visual acuity estimated from the photorefraction test may not be a valid estimate, and the subject can be re-examined or referred for a more thorough examination.

Although the foregoing refers to lines of an eye chart, it is also an option to present only a single symbol of the eye chart line of interest rather than presenting the entire line of symbols.

If the apparatus is used in connection with quickly screening a large number of subjects, the above described option of presenting an entire eye chart and asking the subject to read lines of progressively smaller symbols may be unacceptably time consuming. Accordingly, presenting the subject with a single line (or single symbol) corresponding to his estimated visual acuity (or presenting him with a more complete chart but asking him to read only the line (or a single symbol) corresponding to his estimated visual acuity) is likely to better serve the goal of screening a large population in a time effective manner. One further advantage of presenting the subject with fewer optotypes rather than more optotypes is that the area of second display 52 is limited and so is better able to accommodate a smaller quantity of optotypes.

Figure 6:
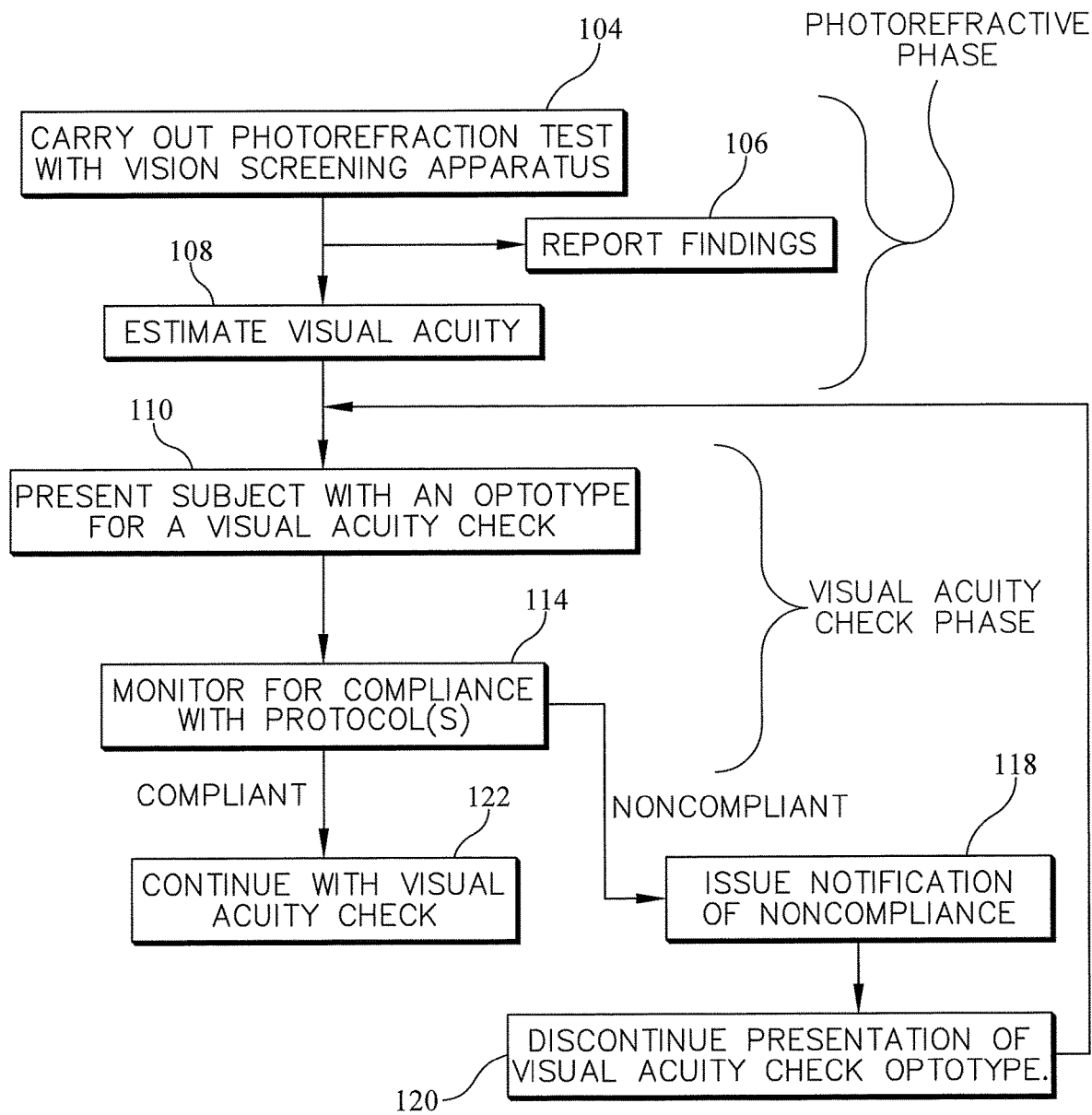
FIG. 6 is a diagram similar to FIG. 5 illustrating operation of an embodiment in which operation of the apparatus is resumed following identification of a noncompliance.

The operation of the apparatus as described in connection with FIG. 6 differs from that of FIG. 5 by providing for resumption or restarting of the visual acuity phase of operation subsequent to a notification of noncompliance. The operation of the apparatus as described in connection with FIG. 7 differs from that of FIG. 5 by providing for the capture of a baseline image in order to guard against compliance being wrongly interpreted as noncompliance. The operation of the apparatus as described in connection with FIG. 8 differs from that of FIG. 5 by automatically distinguishing between the detection of two eyes and one eye, determining which eye has been detected if only one is detected, and reporting that two eyes have been detected or which one of only one eye has been detected. The enhancements of FIGS. 6, 7 and 8 are not mutually exclusive. They can be used individually or in any combination.

Figure 9:
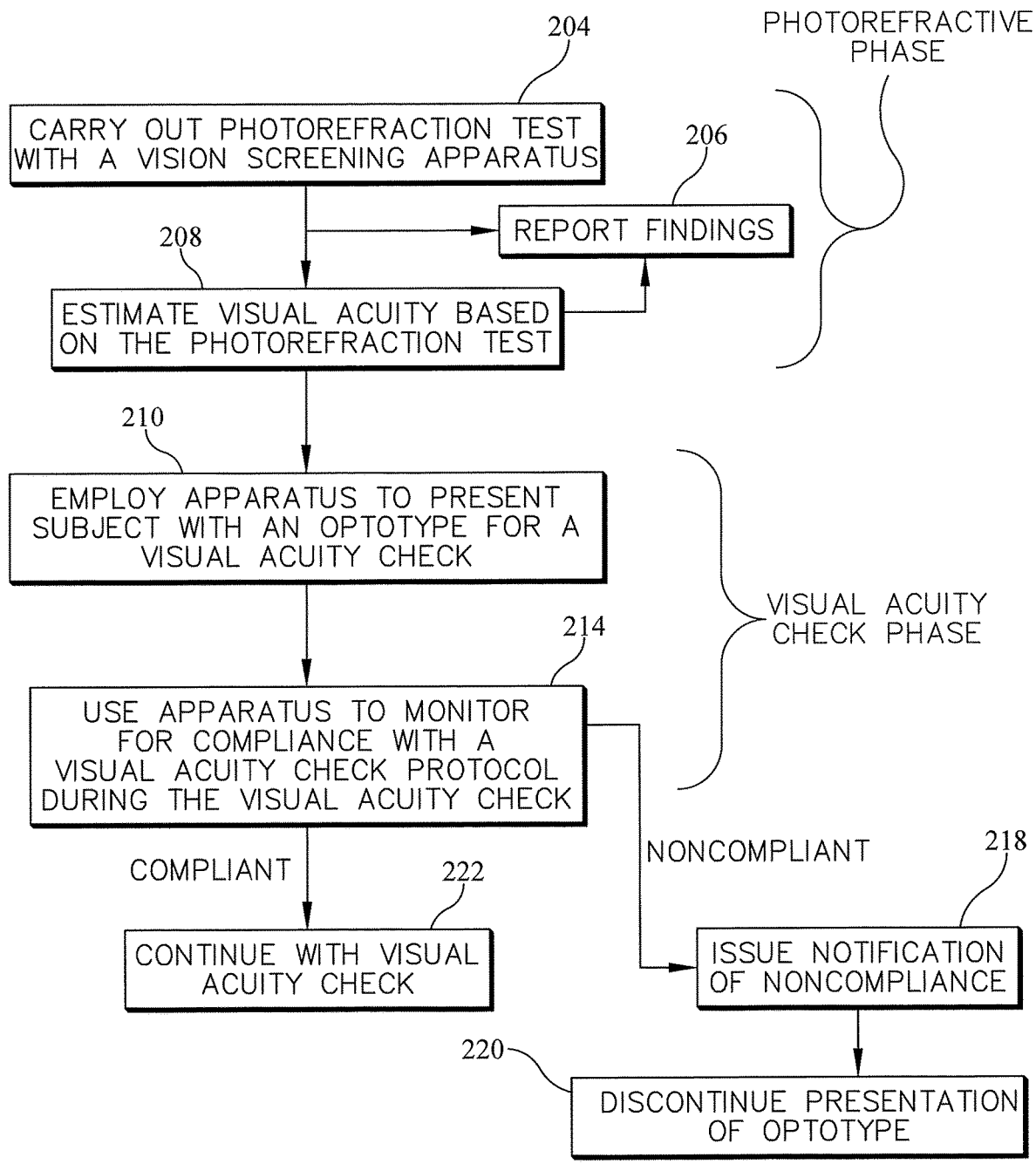
FIG. 9 is a flow chart of a method of visual acuity screening of a subject with a vision screening apparatus including monitoring for and identifying noncompliance with a protocol during a visual acuity phase of the method and issuing a notice of any identified noncompliance.

FIG. 9 illustrates a method of visual acuity screening of a subject with a vision screening apparatus. At block 204 the method carries out a photorefraction test on a subject with the apparatus. At block 208 the method estimates the subject's visual acuity based on the photorefraction test. At block 210 the method employs the apparatus to present the subject with an optotype in order to conduct a visual acuity check. At block 214 the method uses the apparatus to monitor for the subject's compliance with a visual acuity check protocol during the conduct of the visual acuity check. As noted above, examples of subject noncompliance include squinting to better see the optotype and not completely occluding one eye despite having been instructed to do so. If noncompliance is identified at block 214, the method advances to block 218 and issues a notification of the noncompliance. The method may also discontinue presentation of the optotype (block 220), however discontinuing the optotype presentation is not required. Otherwise the method advances to block 222 and continues to present the optotype, thereby continuing the visual acuity check.

Monitoring step 214 may be conducted by using the vision screening apparatus to monitor for whether the subject is using more than one eye while undergoing the visual acuity check, despite having been instructed to use only one eye. This may be carried out by the pupil detection system of the apparatus, i.e. by analyzing an acquired image of the subject to detect how many pupils are present in the image, thereby determining if the pupil detection system has detected just one pupil or two pupils.

Alternatively or additionally, monitoring step 214 may be conducted by using the apparatus to monitor for whether the subject is squinting while undergoing the visual acuity check. This may be carried out by analyzing an acquired image of the subject to detect if the subject is squinting.

Figure 10:
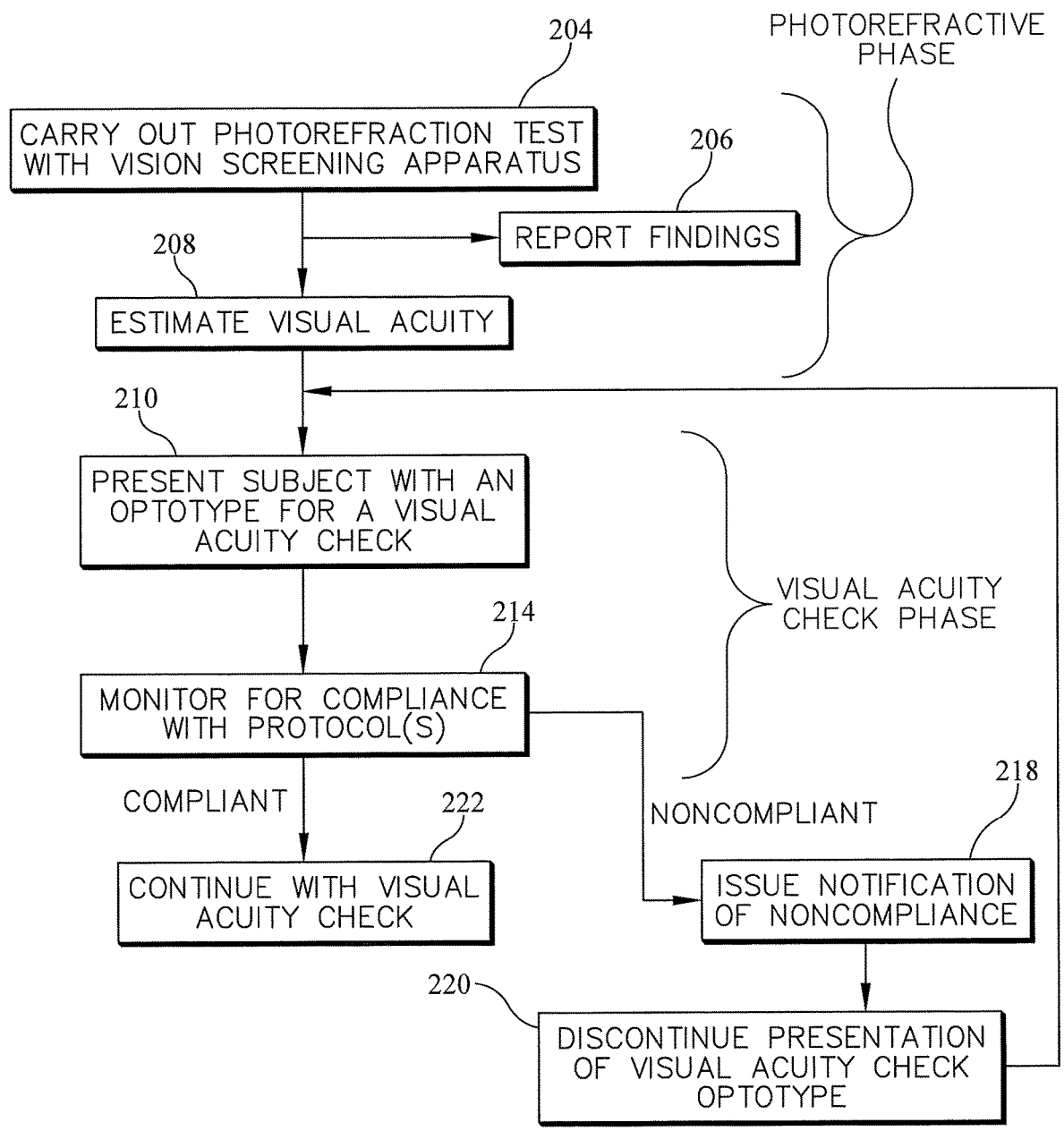
FIG. 10 is a flow chart similar to FIG. 9 illustrating operation of an embodiment of the method in which the visual acuity check is resumed after identification of a noncompliance.

FIG. 10 shows another embodiment of the method. The method steps of FIG. 10 are the same as those of FIG. 9 except that the method of FIG. 10 provides for resuming or restarting the visual acuity check by branching from block 220 back to block 210. Resuming the visual acuity check means starting at or just before whatever point the check had progressed to at the time the noncompliance was identified at block 214. Restarting the visual acuity check means starting the check from its beginning. Either way steps 204 and 208 are not repeated. Between the time of noncompliance identification at block 214 and the time the visual acuity check is restarted or resumed, the examiner corrects the noncompliant condition. The method of FIG. 10 also includes the step of discontinuing the presentation of the visual acuity test optotype to the subject (block 220) and shows the path back to block 210 originating at block 220. However the discontinuation of block 220 need not be included, in which case the branch would originate at block 218.

Figure 11:
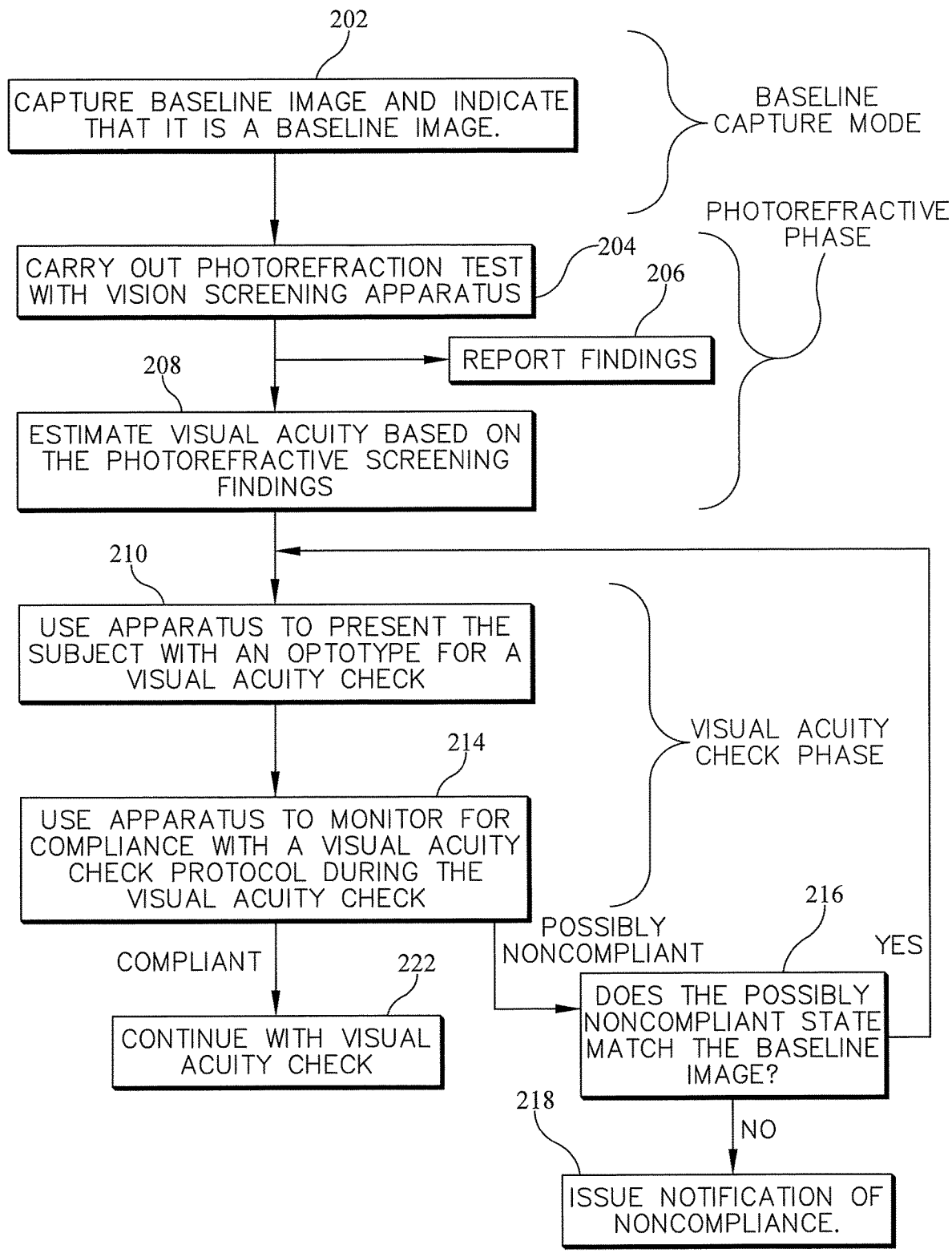
FIG. 11 is a diagram similar to FIG. 9 illustrating operation of an embodiment of the method which refrains from identifying noncompliance in an image that might otherwise be consistent with or at least suggestive of noncompliance.

FIG. 11 shows another embodiment of the method. The method steps of FIG. 11 are the same as those of FIG. 9 except that the method of FIG. 11 includes block 202 which provides for capturing a baseline image of the subject. As noted in connection with the foregoing description of the visual screening apparatus, the baseline image is useful for distinguishing between an image that shows an actual noncompliance and an image that mimics noncompliance but is actually compliant. FIG. 11 also differs from FIG. 9 by treating an identification of noncompliance at block 214 as a possible noncompliance rather than a definite noncompliance, and branching to block 216. At block 216 the method resolves the question of compliance vs. noncompliance by determining if the previously acquired baseline image matches the non-baseline image that caused the method to branch to block 216. If the method determines that the images match it branches back to step 210. Otherwise it branches to step 218 and issues a notification of noncompliance.

Figure 12:
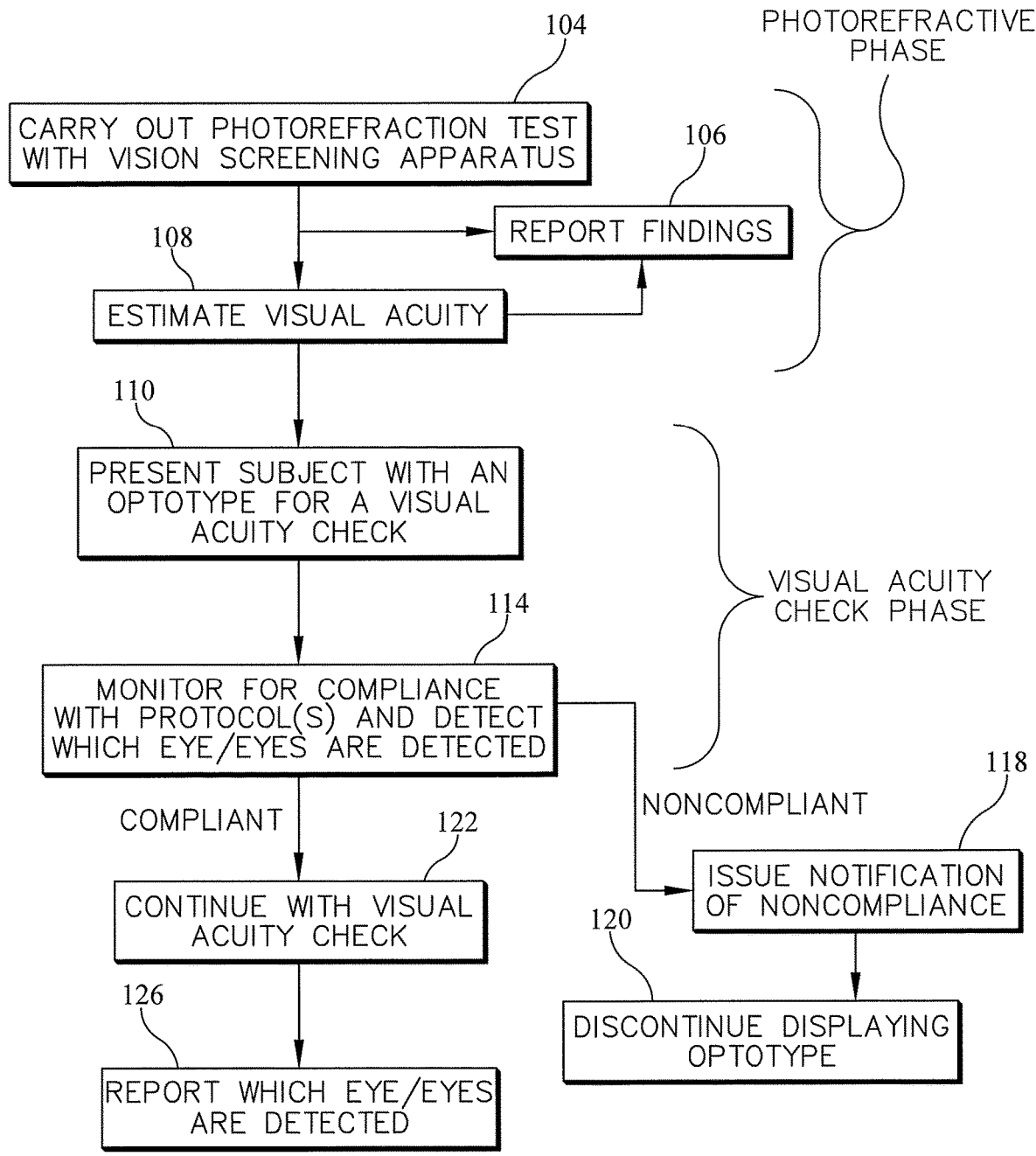
FIG. 12 is a diagram similar to FIG. 9 illustrating operation of an embodiment of the method which detects if one or two of the subject's eyes is present and, if only one eye, which one.

FIG. 12 shows another embodiment of the method. The method steps of FIG. 12 are the same as those of FIG. 9 except that the method of FIG. 12 includes, at step 114, the additional action of detecting if two eyes are detected or which eye, left or right, is detected if only one eye is detected. The method of FIG. 12 also includes block 126 which reports the outcome of the eye detection of block 114.

The enhancements of FIGS. 10, 11 and 12, like those of FIGS. 6, 7 and 8, are not mutually exclusive. They can be used individually or in any combination.

Although this disclosure refers to specific embodiments, it will be understood by those skilled in the art that various changes in form and detail may be made without departing from the subject matter set forth in the accompanying claims.

We claim:

1. A vision screening apparatus, comprising:
a first display unit;
a second display unit;
a processor; and
instructions which, when executed by the processor, cause the apparatus to:
carry out a photorefraction test of a subject;
estimate the subject's visual acuity based on the photorefraction test;
present the subject with a visual acuity check optotype for an interval of time;
monitor for noncompliance with a visual acuity check protocol during at least part of the time interval; and
if a noncompliance is identified, issue a notification, wherein the instructions are adapted, in response to identification of the noncompliance, to cause the apparatus to:
discontinue presenting the subject with the visual acuity check optotype and;
subsequently perform the presenting and monitoring actions without first repeating the carrying out and estimating actions.

2. The apparatus of claim 1 wherein the noncompliance monitored for is at least one of A) the subject's use of more than one eye to discern the optotype, or B) the subject squinting to discern the optotype.

3. The apparatus of claim 2 wherein the instructions cause the apparatus to identify the subject's use of more than one eye by detecting more than one pupil in an image, and the instructions cause the apparatus to identify squinting by detecting an irregularity in the image or in a different image.

4. The apparatus of claim 1 wherein the instructions:
cause the apparatus to recognize a baseline image of one or both of the subject's pupils as characteristic of the subject; and
if a non-baseline image matches the baseline image, causing the apparatus to refrain from identifying possible noncompliance in the non-baseline image as an actual noncompliance.

5. A method of visual acuity screening of a subject with a vision screening apparatus, comprising:
carrying out a photorefraction test with the apparatus;
estimating the subject's visual acuity based on the photorefraction test;
employing the apparatus to present the subject with an optotype in order to conduct a visual acuity check;
using the apparatus to monitor for noncompliance with a visual acuity check protocol during the conduct of the visual acuity check; and
in response to identifying noncompliance:
issuing a notification of thereof,
discontinue presenting the subject with the visual acuity check optotype, and
subsequently using the apparatus to perform the presenting and monitoring actions without first repeating the carrying out and estimating actions.

6. The method of claim 5 wherein if a protocol violation is not identified, continuing with the visual acuity check.

7. The method of claim 5 including:
discontinuing presenting the subject with the optotype; and
subsequent to the step of discontinuing, resuming or restarting the visual acuity check.

8. The method of claim 5 wherein the step of using the apparatus to monitor for noncompliance comprises at least one of:
A) using the apparatus to monitor for whether the subject is using more than one eye while undergoing the visual acuity check; and
B) using the apparatus to monitor for whether the subject is squinting while undergoing the visual acuity check.

9. The method of claim 5 wherein the step of using the apparatus to monitor for noncompliance comprises one or both of:
A) detecting more than one pupil in an image, and
B) detecting squinting in the same image or in a different image.

10. The method of claim 5 wherein the step of using the apparatus to monitor for noncompliance comprises one or both of:
A) analyzing an acquired image to detect how many pupils are present in the image; and
B) analyzing the acquired image or a different acquired image to detect if the subject is squinting.

11. The method of claim 5 comprising:
acquiring a baseline image of one or more of the subject's pupils;
using the apparatus to monitor a non-baseline image for noncompliance with the visual acuity check protocol during the conduct of the visual acuity check; and
if the non-baseline image matches the baseline image, refraining from issuing the notification of noncompliance.

12. A vision screening apparatus, comprising:
a housing;
a display unit disposed on a first side of the housing;
a processor operably connected to the display unit; and
instructions which, when executed by the processor, cause the apparatus to:
carry out a photorefraction test of a subject;
estimate the subject's visual acuity based on the photorefraction test;
recognize a baseline image of one or both of the subject's pupils as characteristic of the subject;
present the subject with a visual acuity check optotype via the display unit;
monitor for noncompliance with a visual acuity check protocol while the visual acuity check optotype is presented to the subject; and
if a non-baseline image matches the baseline image, refrain from identifying possible noncompliance in the non-baseline image as an actual noncompliance with the visual acuity check protocol.

13. The vision screening apparatus of claim 12, wherein the instructions are further adapted, in response to identification of the actual noncompliance, to cause the apparatus to:
discontinue presenting the subject with the visual acuity check optotype and;
subsequently perform the presenting and monitoring actions without first repeating the carrying out and estimating actions.

14. The vision screening apparatus of claim 12, wherein the noncompliance monitored for is at least one of A) the subject's use of more than one eye to discern the optotype, or B) the subject squinting to discern the optotype.

15. The vision screening apparatus of claim 12, wherein the instructions cause the apparatus to identify the subject's use of more than one eye to discern the optotype by detecting more than one pupil in an image, and the instructions cause the apparatus to identify squinting to discern the optotype by detecting an irregularity in the image or in a different image.

16. The vision screening apparatus of claim 12, wherein the display unit comprises a first display unit, the apparatus further comprising a second display unit separate from the first display unit and operably connected to the processor, the second display unit being disposed on a second side of the housing opposite the first side.

17. The vision screening apparatus of claim 16, further comprising a memory on which the instructions are stored, wherein the processor and the memory are disposed within the housing.

18. The vision screening apparatus of claim 16, wherein the second display unit is configured to display a user interface, the user interface comprising a screen that indicates information comprising:
   a pupillary distance of the subject,
   a pupil size of the subject,
   sphere of the subject,
   a cylinder of the subject,
   an axis of the subject, and
   a result of a vision screening procedure that includes the carrying out, estimating, presenting, and monitoring actions.

19. The vision screening apparatus of claim 18, wherein the screen of the user interface comprises a first screen, the first screen displaying the information together with an image of the eyes of the subject.

\* \* \* \* \*